(12) United States Patent
Bjorkholm

(10) Patent No.: US 7,317,782 B2
(45) Date of Patent: Jan. 8, 2008

(54) RADIATION SCANNING OF CARGO CONVEYANCES AT SEAPORTS AND THE LIKE

(75) Inventor: Paul Bjorkholm, Newport Beach, CA (US)

(73) Assignee: Varian Medical Systems Technologies, Inc., Palo Alto, CA (US)

(*) Notice: Subject to any disclaimer, the term of this patent is extended or adjusted under 35 U.S.C. 154(b) by 35 days.

(21) Appl. No.: 10/356,101

(22) Filed: Jan. 31, 2003

(65) Prior Publication Data
US 2004/0156477 A1 Aug. 12, 2004

(51) Int. Cl.
G01N 23/04 (2006.01)
(52) U.S. Cl. .................................. 378/57; 378/193
(58) Field of Classification Search .............. 378/57, 378/58, 62, 193–198
See application file for complete search history.

(56) References Cited

U.S. PATENT DOCUMENTS

| | | | |
|---|---|---|---|
| 3,158,744 A * | 11/1964 | Bernstein | 378/58 |
| 3,543,952 A | 12/1970 | Young | |
| 3,559,822 A | 2/1971 | Lichtenford | |
| 3,630,390 A | 12/1971 | Tax | |
| 3,812,987 A | 5/1974 | Watatani | |
| 3,881,608 A | 5/1975 | Hupkes | |
| 3,921,818 A | 11/1975 | Yamagishi | |
| 4,244,615 A | 1/1981 | Brown | |
| 4,400,650 A | 8/1983 | Giebeler, Jr. | |
| 4,430,568 A | 2/1984 | Yoshida et al. | |
| 4,599,740 A | 7/1986 | Cable | |
| 4,726,046 A | 2/1988 | Nunan | 378/65 |
| 5,065,418 A | 11/1991 | Bermbach et al. | |
| 5,098,640 A | 3/1992 | Gozani et al. | |
| 5,111,494 A | 5/1992 | Turner et al. | |
| 5,124,658 A | 6/1992 | Adler | |
| 5,251,240 A | 10/1993 | Grodzins | |
| 5,251,768 A | 10/1993 | Yoshimatsu et al. | 212/277 |
| 5,422,926 A | 6/1995 | Smith et al. | |
| 5,495,106 A | 2/1996 | Mastny | |
| 5,524,133 A | 6/1996 | Neale et al. | 378/53 |

(Continued)

FOREIGN PATENT DOCUMENTS

CN 2354135 Y 12/1999

(Continued)

OTHER PUBLICATIONS

McDonald Marci, Checkpoint Terror, U.S. News & World Report, Feb. 11, 2002, p. 52, USA.

(Continued)

*Primary Examiner*—Craig E. Church
(74) *Attorney, Agent, or Firm*—Brandon N. Sklar; Kaye Scholer LLP

(57) ABSTRACT

A radiation scanning system comprises a radiation source and a radiation detector that are proximate a crane system that moves objects between the source and the detector for scanning. The source and/or detector may be supported by the crane system or may be near to the crane system. Preferably, the source and detector are supported by the crane system or they are within a profile defined by the crane system. The radiation scanning system is particularly suited to scan cargo conveyances, such as sea cargo conveyances, as they are being removed from or loaded onto a ship. Methods of examining objects are disclosed, as well.

72 Claims, 9 Drawing Sheets

U.S. PATENT DOCUMENTS

| | | | |
|---|---|---|---|
| 5,638,420 A | 6/1997 | Armistead | |
| 5,692,028 A | 11/1997 | Geus et al. | |
| 5,784,430 A | 7/1998 | Sredniawski | |
| 5,809,106 A | 9/1998 | Kitade et al. | 378/132 |
| 5,838,759 A | 11/1998 | Armistead | |
| 5,848,115 A | 12/1998 | Little et al. | 378/4 |
| 5,910,973 A * | 6/1999 | Grodzins | 378/57 |
| 5,917,880 A | 6/1999 | Bjorkholm | |
| 5,948,137 A | 9/1999 | Pflaum | |
| 6,009,146 A | 12/1999 | Adler et al. | |
| 6,058,158 A | 5/2000 | Eiler | |
| 6,115,128 A | 9/2000 | Vann | |
| 6,192,104 B1 | 2/2001 | Adams et al. | |
| 6,234,332 B1 | 5/2001 | Monzen et al. | |
| 6,282,262 B1 | 8/2001 | Warburton | |
| 6,292,533 B1 | 9/2001 | Swift et al. | |
| 6,301,326 B2 | 10/2001 | Bjorkholm | |
| 6,356,620 B1 | 3/2002 | Rothschild et al. | |
| 6,366,021 B1 | 4/2002 | Meddaugh et al. | |
| 6,370,222 B1 | 4/2002 | Cornick, Jr. | |
| 6,445,766 B1 | 9/2002 | Whitham | |
| 6,448,564 B1 | 9/2002 | Johnson et al. | |
| 6,453,007 B2 | 9/2002 | Adams et al. | |
| 6,459,761 B1 | 10/2002 | Grodzins et al. | |
| 6,495,837 B2 | 12/2002 | Odom et al. | |
| 6,542,580 B1 * | 4/2003 | Carver et al. | 378/57 |
| 6,553,094 B1 * | 4/2003 | Bernardi et al. | 378/57 |
| 6,580,940 B2 | 6/2003 | Gutman | 600/427 |
| 6,628,745 B1 | 9/2003 | Annis et al. | |
| 6,778,631 B2 * | 8/2004 | Franke | 378/57 |
| 6,778,633 B1 | 8/2004 | Loxley et al. | 378/113 |
| 6,813,336 B1 | 11/2004 | Siochi | 378/65 |
| 6,936,820 B2 | 8/2005 | Peoples | 250/336.1 |
| 7,162,005 B2 | 1/2007 | Bjorkholm | 378/57 |
| 2003/0108150 A1 | 6/2003 | Franke | 378/57 |
| 2003/0108405 A1 | 6/2003 | Takehara et al. | 414/140.3 |

FOREIGN PATENT DOCUMENTS

| | | |
|---|---|---|
| CN | 1392404 A | 1/2003 |
| WO | WO 03/053840 A1 | 7/2003 |

OTHER PUBLICATIONS

Shapiro, Carolyn, "Terminals install radiation-detection equipment," The Virginian-Pilot, Dec. 21, 2002, available at http://hamptonroads.com/supersearch/articles/print.cfm?id=48036.

Seigle, Greg, "U.S. Response I: Customs Seeks to Reverse Shipping Inspection Procedures," Jan. 18, 2002, NTI: Global Security Newswire, available at http://www.nti.org/d_newswire/issues/2002/1/18/1s.html.

Bonner, Robert C., "Speech Before the Center for Strategic and International Studies (CSIS), Washington, D.C.," Jan. 17, 2002, Speech to the 2001 National High Intensity Trafficking Areas (HIDTA) Conference (Best Copy).

Aston, Adam; Cady John, "Pandora's Cargo Boxes," Business Week, Oct. 22, 2001, New York.

De Moulpied, David S., Waters, David, "Cargo Screening Techniques Become More Widely Accepted," pp. 127-129, , Port Technology International, Tenth Edition, 1999.

\* cited by examiner

RADIATION SCANNING OF CARGO CONVEYANCES AT SEAPORTS AND THE LIKE

FIELD OF INVENTION

Radiation scanning of objects, and more particularly, radiation scanning of cargo conveyances for contraband.

BACKGROUND OF INVENTION

Radiation is commonly used in the non-invasive inspection of objects such as luggage, bags, briefcases, and the like to identify hidden contraband. Contraband includes guns, knives, explosive devices, as well as illegal drugs, for example. As criminals and terrorists have become more creative in the way they conceal contraband, the need for more effective non-invasive inspection techniques has grown. While the smuggling of contraband onto planes in carry-on bags and in luggage has been a well-known, on-going concern, a less publicized but also serious threat is the smuggling of contraband across borders and by boat in large cargo containers. Only 2%-10% of the 17 million cargo containers brought to the United States by boat are inspected. "Checkpoint Terror", U.S. News and World Report, Feb. 11, 2002, p. 52.

One common inspection system is a line scanner, where an object to be inspected, such as luggage, is passed between a stationary source of radiation, such as X-ray radiation, and a stationary detector. The radiation is collimated into a vertical fan beam or a pencil beam and the object is moved horizontally through the beam. The radiation transmitted through the object is attenuated to varying degrees by the contents of the object. The attenuation of the radiation is a function of the density of the materials through which the radiation beam passes. The attenuated radiation is detected and radiographic images of the contents of the objects are generated for inspection. The radiographic image reveals the shape, size, and varying densities of the contents.

In a typical seaport environment, a cargo ship is docked in the seaport, and containers are lifted off from the ship by a crane. The containers may be lowered by the crane onto a truck. If it is decided to inspect the container for contraband then the truck takes the container to a designated inspection site.

Typical X-ray inspection systems, when used in a seaport or airport environment, are impractical due to the size of the cargo containers. Standard cargo containers are typically 20-50 feet long (6.1-15.2 meters), 8 feet high (2.4 meters) and 6-9 feet wide (1.8-2.7 meters). Air cargo containers, which are used to contain a plurality of pieces of luggage or other cargo to be stored in the body of an airplane, may range in size (length, height, width) from about 35×21×21 inches (0.89×0.53×0.53 meters) up to about 240×118×96 inches (6.1×3.0×2.4 meters). Sea cargo containers are typically about 40-50 feet long, 8 feet wide and 8 feet high (12.2-15.2×2.4×2.4 meters). Large collections of objects, such as many pieces of luggage, may also be supported on a pallet. Pallets, which may have supporting side walls, may be of comparable sizes as cargo containers. The term "cargo conveyance" is used herein to encompass cargo containers (including sea cargo containers) and pallets.

Fixed inspection systems have been proposed for inspecting large containers. For example, U.S. Pat. No. 4,430,568 to Yoshida discloses an X-ray system for the inspection of packages, including large shipping containers. A conveyor moves the package or container horizontally between the X-ray source supported on a floor and a detector array. Similarly, U.S. Pat. No. 4,599,740 to Cable discloses a fixed inspection system, where an X-ray source transmits a continuous beam of radiation across a conveyor along which the containers to be inspected are moved. The container may be moved either continuously or incrementally. The radiation transmitted through a container is detected by a "folded" sensor screen or device having two, perpendicular arms, one extending vertically along a side of the container and the other extending horizontally over the top of a container during inspection. The folded sensor enables the system to have a smaller height than would otherwise be necessary in order to detect radiation transmitted through the entire container.

It has also been proposed to scan large containers with portable X-ray imaging systems. For example, U.S. Pat. No. 5,638,420 to Armistead discloses a straddle inspection system, whereby the radiation scanning system (a source and detector) is fixed to a movable frame and the frame is moved horizontally along the length of the container while the image data is sequentially recorded. Also, U.S. Pat. No. 5,692,028 to Geus et al. discloses an X-ray inspection system including a source and a detector that are mounted on a motor vehicle. The vehicle is driven past the object in order to scan the contents of the object. It has been proposed to inspect sea containers with such systems.

The systems described above have several disadvantages. For example, the systems take up valuable space in the sea port. While the Armistead and Geus patents were designed to be portable in order to minimize the amount of space permanently dedicated to the X-ray facility, both of these systems are still large and establish a large exclusion zone when in use. In addition, all of these systems may be easily defeated within the "large container" environment. For example, once a container is unloaded from the ship and placed on the dock for delivery to the inspection station, contraband can be easily removed before inspection. The above described systems also have slow inspection speeds. The containers can be typically unloaded from a ship more rapidly than the scanner can complete its inspection. Therefore, there is still a need for improved inspections systems for sea containers at a sea port.

It has also been proposed to mount a radiation detector on a crane system, to detect radiation emitted by radioactive materials within a cargo conveyance being moved by the crane system. Such systems cannot detect contraband that is not radioactive or is shielded.

SUMMARY OF THE INVENTION

In one embodiment of the invention, a radiation scanning system comprises a radiation source, such as source of X-ray radiation, and a radiation detector that are proximate a crane system that moves objects, such as cargo and sea containers and other cargo conveyances, from one location to another. Here, a "crane system" may be any system that lifts an object from a first location and lowers the object onto a second, different location. The crane system moves the object through a space between the source and the detector so that the object may be scanned. The crane system may move objects, such as sea containers and other types of cargo conveyances, off of and onto a ship at a seaport, for example. The source and/or detector may be supported by the crane system or may be near to the crane system, supported on the ground, for example. The term "proximate" here means supported by or near to. The term "near to" as used herein means any location to which the crane is capable of passing an object. If not supported by the crane system, the source and/or detector are preferably within a profile defined by the crane system, so that no additional space is taken up by the radiation scanning system.

In the context of a seaport, an object being unloaded from a ship may be lowered through a radiation beam emitted by the source and detected by the detector, for example. Alternatively, objects being loaded onto a ship may be lifted from the seaport and raised through the radiation beam, while being loaded onto a ship. The system enables the examination of large cargo conveyances during the loading and unloading, without requiring that the conveyances be taken to an isolated examining facility. Additionally, since in this embodiment the radiation source and detector are preferably supported by or within the profile of the crane system, no more space is taken up by the system, than the space already taken up by the crane system, itself.

DETAILED DESCRIPTION OF THE PREFERRED EMBODIMENTS

Figure 1A:
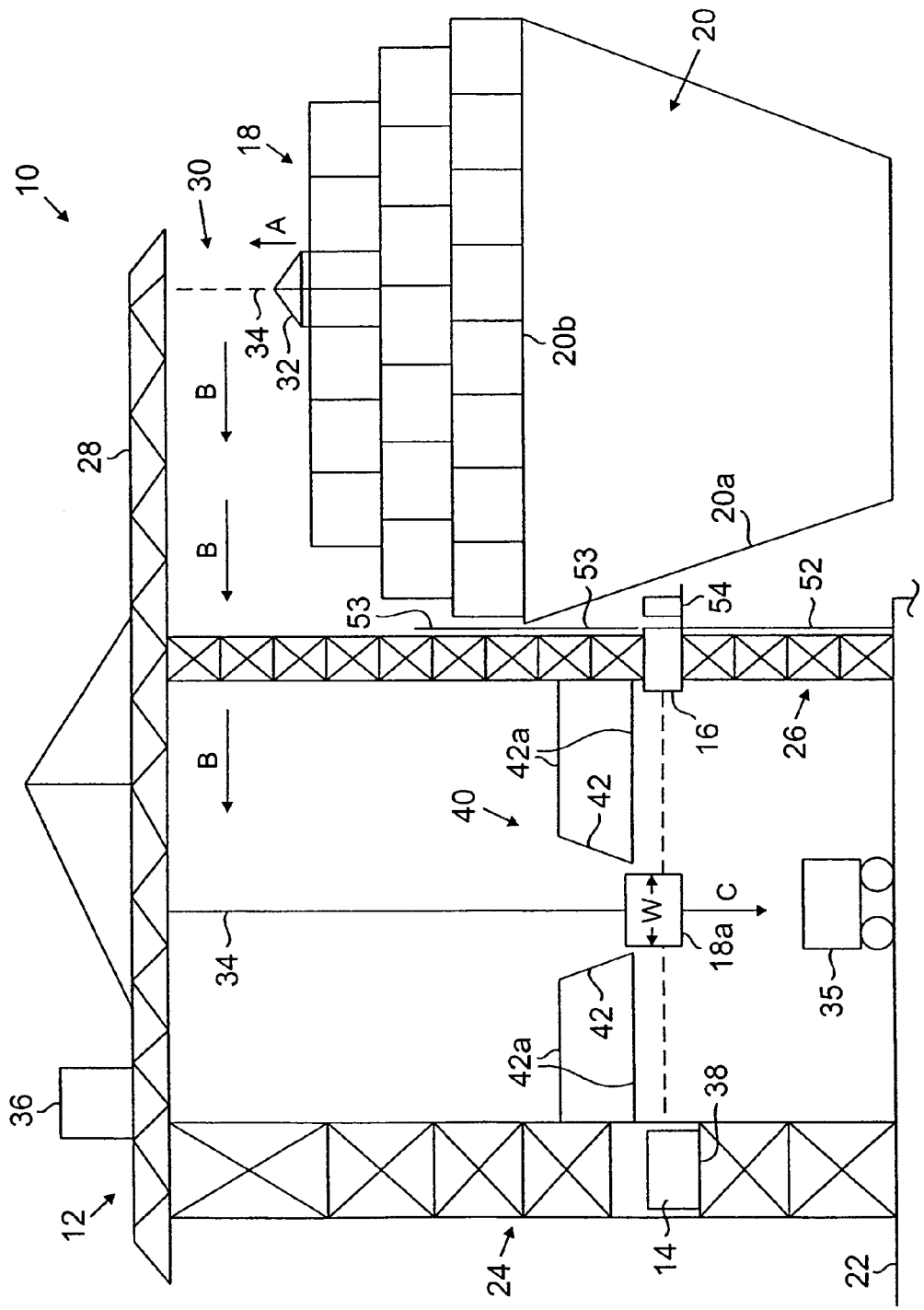
FIG. 1a is a schematic representation of a radiation scanning system supported by a crane system in accordance with one embodiment of the invention.

FIG. 1a is a schematic representation of a radiation scanning system 10 in accordance with one embodiment of the present invention. In this embodiment, the system 10 comprises a crane system 12 supporting a radiation source 14 and a radiation detector 16. The crane system 12 may be a standard crane for unloading and loading cargo conveyances 18, such as sea containers and pallets, for example, from a ship 20 at a seaport 22, as is known in the art. In accordance with the present invention, the crane system 12 may be any device used to lift an object from one location and lower the object onto another location.

The crane system 12 comprises opposing vertical structures 24, 26 supporting a boom arm 28. A conveying system 30 is supported by the boom arm 28. The conveying system 30, the details of which are not shown but are known in the art, may comprise a carriage or spreader bar 32 for securing a cargo conveyance 18 or other such object. The carriage 32 is suspended from a chain or metal rope 34 driven around pulleys by a motor (not shown). The conveying system 30 may lift a cargo conveyance 18 via the carriage 32 off of a ship vertically, as indicated by arrow A, move the cargo conveyance horizontally towards the seaport 22, as indicated by arrows B, and lower the cargo conveyance onto a truck 35, or onto the seaport, itself, as indicated by arrow C. The crane system 12 may be operated by an operator located in a control compartment 36, for example. The carriage 32 is released and returned by the conveying system 30 to the ship 20, to be secured to another cargo conveyance 18. The process is reversed to load cargo conveyances 18 onto the ship 20.

Figure 1B:
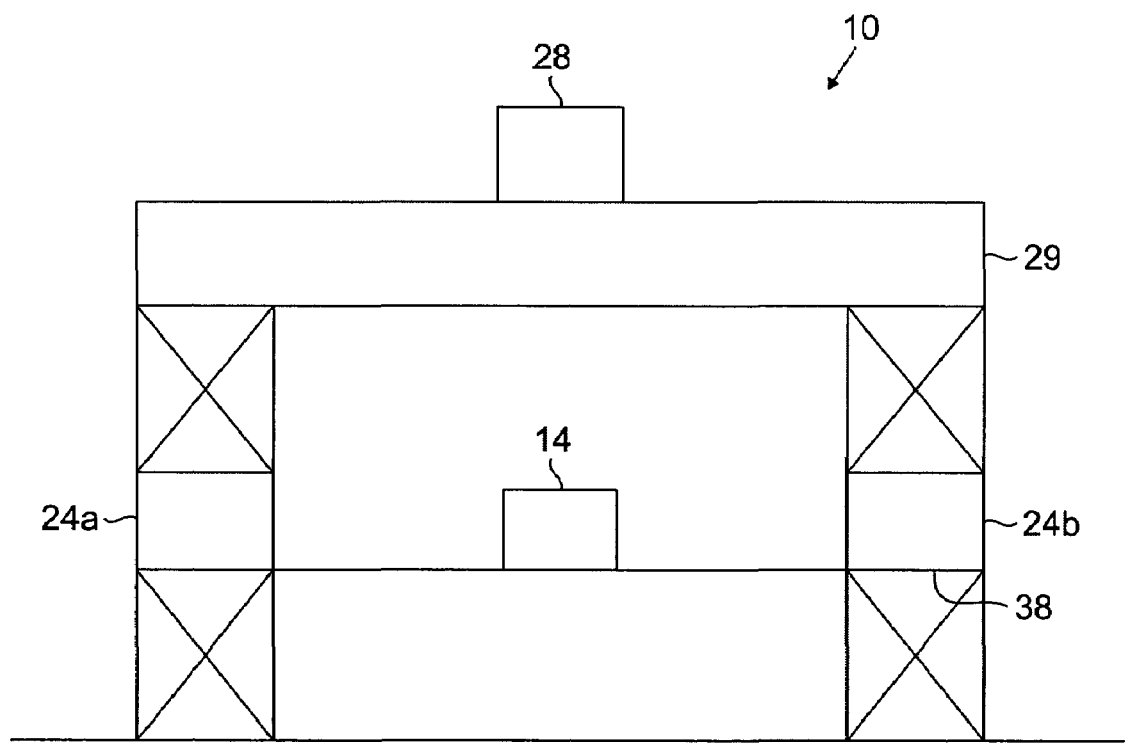
FIG. 1b is a rear view of the radiation scanning system of FIG. 1.

FIG. 1b is a rear view of the radiation scanning system 10, showing the source 14 supported on a crossbeam 38 (also shown in FIG. 1a) connecting a pair of vertical supports 24a, 24b of vertical structure 24. The detector 16, not shown in this view, is similarly supported on a cross beam between vertical supports of vertical structure 26. The guide 40 and the ship 20 are also not shown in this view. The source 14 and the detector 16 are separated by a sufficient distance for a cargo conveyance 18 or other such object to be lowered between them. Also shown in this view is an upper crossbeam 29 that supports the boom arm 28.

The radiation source 14 and detector 16 may be supported by an existing cross-beam or additional cross-beams and accompanying supporting structure may be added to support the source and/or the detector, depending on the size and structure of the crane system 12 and the desired distance between the source and the detector, for example. A standard crane system 12 may be readily retrofit to include the source 14 and the detector 16.

While the cargo conveyance 18 is being moved between the source 14 and the detector 16 (either raised or lowered), the source emits a radiation beam 43 onto a face 18a of the cargo conveyance 18. The detector 16 detects radiation transmitted through the cargo conveyance 18. By moving the cargo conveyance 18 completely through the beam, the entire conveyance may be scanned.

Preferably, the radiation beam 43 is a horizontally diverging beam. More preferably, the radiation beam is a horizontally diverging fan beam. A cone beam may be used, as well. Here, the term "fan beam" refers to a diverging radiation beam having essentially only one dimension, such as a horizontal direction. The term "cone beam" refers to a two dimensional diverging radiation beam, such as a radiation beam that diverges horizontally and vertically. The cone beam need not be a mathematical cone; it may be an arbitrarily shaped cone with a cross-section having an outer edge with a rectangular, square, circular or elliptical shape, for example. The radiation beam may be a rectangular asymmetric cone beam, for example. The horizontally diverging beam 43 may be defined by one or more collimators, as is known in the art. The collimator may be integrated with the source 14.

A guide 40 comprising tapered walls 42 may be provided proximate the source 14 and the detector 16 to help guide the cargo conveyance 18 as it is being moved between the source 14 and the detector 16. If the cargo conveyance 18 is scanned as it is being lowered, as in the embodiment of FIG. 1a, the guide 40 is above the level of the source 14 and detector 16. If the cargo conveyance 18 is scanned while it is being raised, the guide 40 is below the level of the source 14 and detector 16. The guide 40 may be supported by horizontal beams 42a attached to the crane's supporting structures 24, 26, for example. One pair of opposing tapered walls 42 are shown in FIG. 1a. A second pair of opposing walls, transverse to the first pair, may be provided, if desired.

Figure 2:
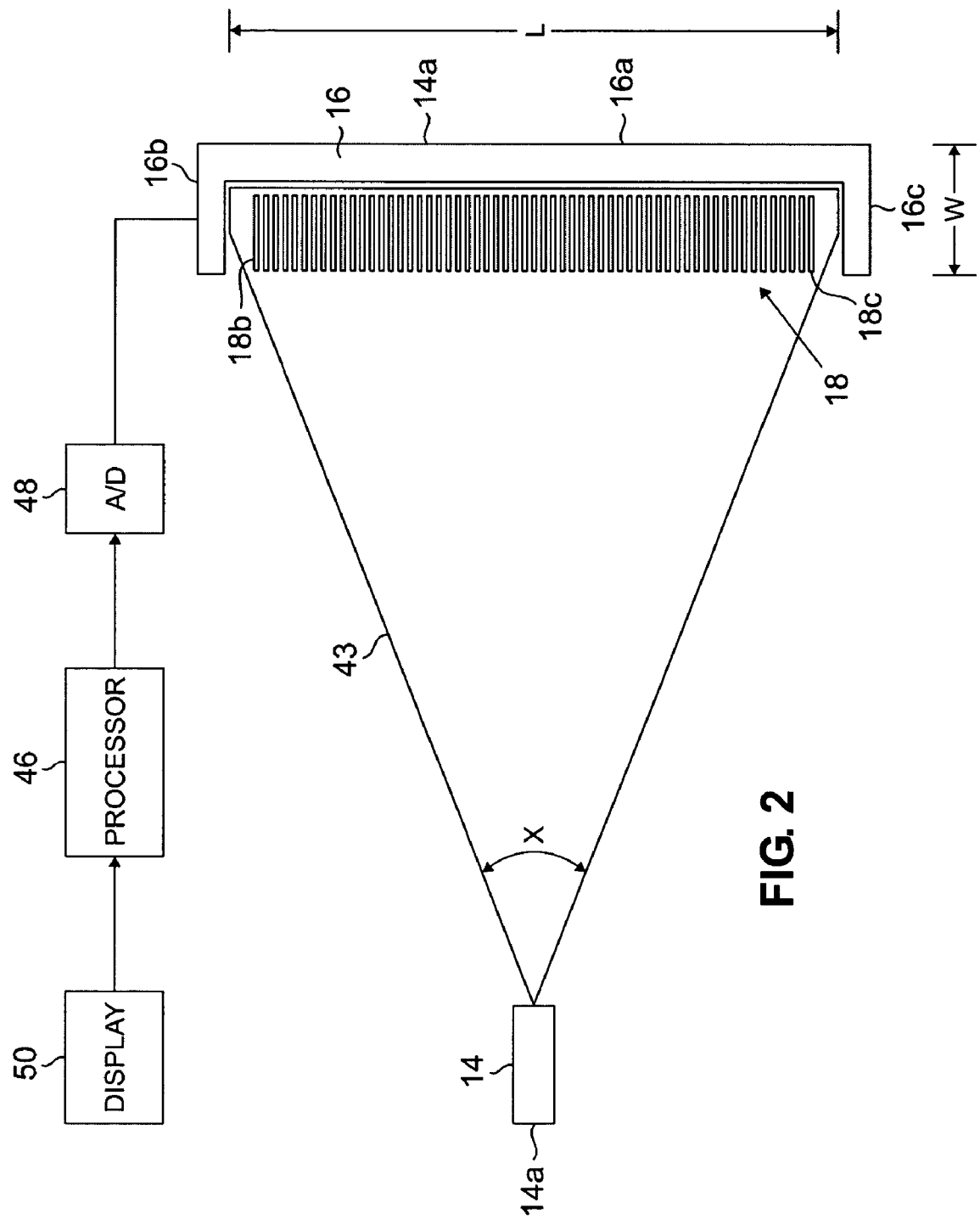
FIG. 2 is a top view of a cargo conveyance being lowered through a radiation beam emitted by a source, such as a linear accelerator, in the embodiment of FIG. 1.

FIG. 2 is a top view of a horizontally diverging radiation beam 43 scanning a cargo conveyance 18 being lowered vertically through the beam. In the prior, art discussed above, in contrast, an object is typically moved horizontally through a vertically diverging beam. The source 14 and detector 16 are shown.

The detector 16 may be a detector array. The detector array 16 may have one long portion 16a behind the cargo conveyance 18 and two short portions 16b, 16c parallel to each other and perpendicular to the long portion 16a. The short portions 16b, 16c face the side walls 18b, 18c of the cargo conveyance 18. The short portions 16b, 16c detect radiation transmitted through the sides 18b, 18c of the cargo conveyance 18. Providing such short, parallel portions enables the detector array 16 to be more compact. Instead of the short parallel portions 18b, 18c, a longer long portion 16a may be provided to capture all the radiation transmitted through the cargo conveyance 18. The detector or detector array 16 may be curved, as well. It may be semi-circular, for example.

The radiation source 14 maybe a source of X-ray radiation, such as Bremsstrahlung radiation, for example. To examine cargo conveyances having a width "W" (see FIG. 1a and FIG. 2) greater than about 5 feet (1.5 meters) by a radiation scanning system 10 in accordance with the embodiment of FIG. 1, the X ray source 14 preferably generates a radiation beam 43 having a peak energy greater than about 1 MeV. More preferably, the X-ray source 14 generates a radiation beam 43 having a peak energy greater than about 6 MeV, for example. The X-ray source 14 may be a linear accelerator, such as a Linatronâ Linear Accelerator ("Linatronâ"), available from Varian Medical Systems, Inc., Palo Alto, CA ("Varian") for example. Other types of X-ray sources may be used as well, such as electrostatic accelerators, microtrons and betatrons, for example. X-ray tubes may also be used, particularly for cargo conveyances and other objects having a width W less than about 5 feet (1.5 meters).

To detect a fan beam, the detector array 16 may be a one dimensional detector array comprising modules of detector elements, as is known in the art. Each one dimensional detector module may comprise a single row of a plurality of detector elements. The detector elements may comprise a radiation sensitive detector, such as a scintillator, and a photosensitive detector, such as a phototube or photodiode, as is known in the art. A high density scintillator, such as a cadmium tungstate scintillator, may be used. The scintillator may have a density of 8 grams per cubic cm, for example. Appropriate cadmium tungstate scintillators are available from Saint Gobain Crystals, Solon, Ohio, U.S.A. and Spectra-Physics Hilger Crystals, Kent, U.K. for example. Detector modules having detection efficiencies of from about 10% to about 80% are preferably used, depending on the radiation spectrum of the radiation beam 43.

Multiple, closely spaced, parallel fan beams may also be defined by one or more collimators. In that case, a row of one dimensional detectors may be provided for each fan beam.

The detector array is electrically coupled to a processor 46, such as a computer, through an analog-to-digital converter 48. The processor 46 reconstructs the data output by the detector array 16 into images which may be displayed on a monitor 50 on site or at another location. While one processor 46 and A/D convertor 48 are shown, additional processors, A/D converters, and other signal processing circuits may be provided, as is known in the art.

If a cone beam is used, the detector array may comprise one or more rows of two dimensional detector modules. A two dimensional detectors module may comprise a plurality of rows and columns of detector elements.

The horizontal length of a horizontally diverging beam 43 at the face 18a of the cargo conveyance 18 may be slightly greater than the width of the conveyance. The vertical height of a fan beam at the face 18a may be from about 2 mm to about 10 mm, for example. If a cone beam is used, it may have a vertical height of from about 200 mm to about 400 mm at the face 18a, for example.

Collimators (not shown) may also be provided between the object and the detector array 16 to block scattered radiation from reaching the detector array 16.

Shielding may be provided as needed. Lead curtain shields 52, 53 may be provided behind the detector 16 to capture scattered radiation. Curtain 53 prevents scattered radiation from crossing the deck 20b of the ship 20, where there may be workers. A radiation stop 54 may be provided behind the detector 16, supported by the crane system 12. The operator compartment 36 may be shielded to protect the operator. Shielding, such as additional lead curtains, may also be provided on the sides of the crane system 12 as well, if desired. The hull 20a of the ship 20 may provide shielding instead of or in addition to the radiation stop 54 and/or at least part of the lengths of the lead curtains 52, 53. An advantage of this embodiment of the invention is that radiation is used in regions that are normally unoccupied, decreasing shielding requirements as compared to at least certain prior art systems.

The radiation scanning system 100 will generally be able to examine cargo conveyances 18 as fast as they can be moved by the crane system 12. For example, if the radiation source is a linear accelerator generating a fan beam having a width of about 5-7 mm at the face 18a of the cargo container 18 and emitting radiation beams at a rate of 300 pulses per second, it would take about 2 seconds to scan a cargo conveyance 18 having a height of about 2.5 meters, with a spatial resolution of about 5 mm.

A radiation beam 43 emitted along a longitudinal axis 14a (shown in FIG. 2) of a typical radiation source 14 has its highest intensity along the axis. The intensity drops rapidly as the angle from this axis 14a increases. It is therefore preferable not to emit a radiation beam of too wide of an angle. For example, it is preferred that the angle of the beam not exceed 30 degrees. In order to illuminate the entire face 18a of a long object, such as a sea container, with a narrow beam, however, the source 14 must be far from the face. Intensity also drops by the square of the distance between the source 14 and the face 18a. In the example of FIG. 2, if the cargo conveyance is a sea container having a length L of 40 feet (12.2 meters) long, a radiation beam 43 emitted over an angle X of about 25 degrees must be about 43 feet (13.1 meters) from the face 18a to illuminate the entire face. The angle X of the radiation beam 43 and the distance between the source and the face 18a are factors to be balanced in the design of the radiation scanning system 10.

Figure 3:
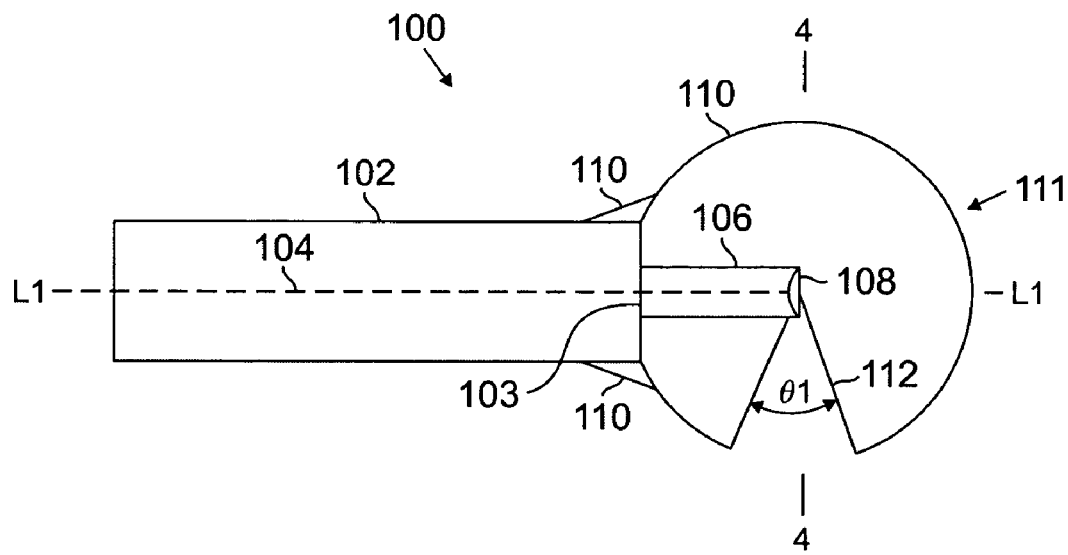
FIG. 3 is a side view of an alternative source for use in the embodiment of FIG. 1.

FIG. 3 shows an alternative configuration for the radiation source 14 that enables the source to be much closer to the cargo conveyance 18, and still illuminate the entire face 18a of a cargo conveyance with a more uniform radiation beam than a beam emitted by the source 14 of FIG. 2. The X-ray source 100 in FIG. 3, referred to as a "panoramic" radiation source, is described in application Ser. No. 10/199,781 filed on Jul. 19, 2002, assigned to the assignee of the present invention and incorporated by reference, herein. The panoramic source 100 comprises a linear accelerator body 102, which may be a Varian Linatron®, as described above, or may have other configurations known in the art. The linear accelerator body 102 has an open output end 103. An electron beam 104, shown in phantom, is accelerated as it follows a path through the linear accelerator body 102 along a longitudinal axis L1 of the body. The electron beam 104 exits the accelerator body from the output end 103. A proximal end of a tube 106, referred to as a drift tube, is connected to the output end 103 of the linear accelerator body 102, in communication with and extending from the open output end. The drift tube 106 may have a diameter of from about 6 to about 10 mm, for example. The drift tube 106 may be the same material as the linear accelerator 102, to facilitate the connection of the drift tube to the linear accelerator body. The drift tube 106 and linear accelerator body 102 may be metal for example. The drift tube and linear accelerator body may be other materials, as well.

A target material 108 of a metal with a high atomic number and a high melting point, such as tungsten or another refractory metal, is provided at the distal end of the drift tube 106. Shielding material 110, such as tungsten, steel or lead, is provided around the drift tube 106, and the target material 108 and may extend over a distal portion of the linear accelerator body 102, as well. The shielding material 110 may be in the shape of a sphere, for example, and the target material 108 may be at the center of sphere, within the drift tube 106. The shielding material 110 may also have other shapes. The drift tube 106, the target material 108 and the shielding material are referred to as a "shielded target 111".

Figure 4:
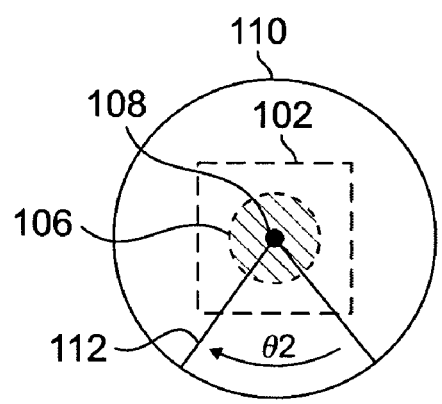
FIG. 4 is a front view of the source of FIG. 3.

A collimating slot 112 extends from the end of the drift tube 106, through the shielding material 110, transverse to the longitudinal axis L1 of the linear accelerator body 102. The slot 112 is shaped to collimate the X-ray beam emitted by the target material into a desired shape, such as into a fan beam or a cone beam, which is emitted from the shielded target in a direction perpendicular to the axis L1 of the accelerator body 102. The slot 112 has a first angular dimension θ1. FIG. 4 is a cross-sectional view of the shielded target 111 through line 4-4 of FIG. 3, showing a second angular dimension θ2 of the slot. The first angular dimension θ1 and the a second angular dimension θ2 define the shape of the radiation beam 43. In a preferred use, the source 100 is oriented so that the first angular dimension θ1 defines the vertical height of the radiation beam 43 and the second angular dimension θ2 defines the horizontal angle of the beam, as shown in FIG. 5, discussed below.

The electron beam 104 emitted by the linear accelerator body 102 along the longitudinal axis L1 passes through the drift tube 106 and impacts the material 108. Bremsstrahlung X-ray radiation is emitted from the target material 108 in all directions. The radiation emitted in the direction of the collimating slot 112 is collimated into the desired shape and emitted from the device 100. The shielding material 110 absorbs radiation emitted in other directions. While the intensity of the radiation emitted perpendicular to the direction of the electron beam impacting the target material may be much less than the intensity of the radiation emitted in the forward direction, by defining the horizontal angle and the beam by the second angular dimension θ2, the radiation emitted across the entire radiation beam 43 has substantially the same intensity. Since the second angular dimension θ2 may be any desired angle up to 180 degrees, the source 100 may be very close to the face 18a of the cargo conveyance 18. The intensity drop due to distance is therefore much less than in other configurations.

Figure 5:
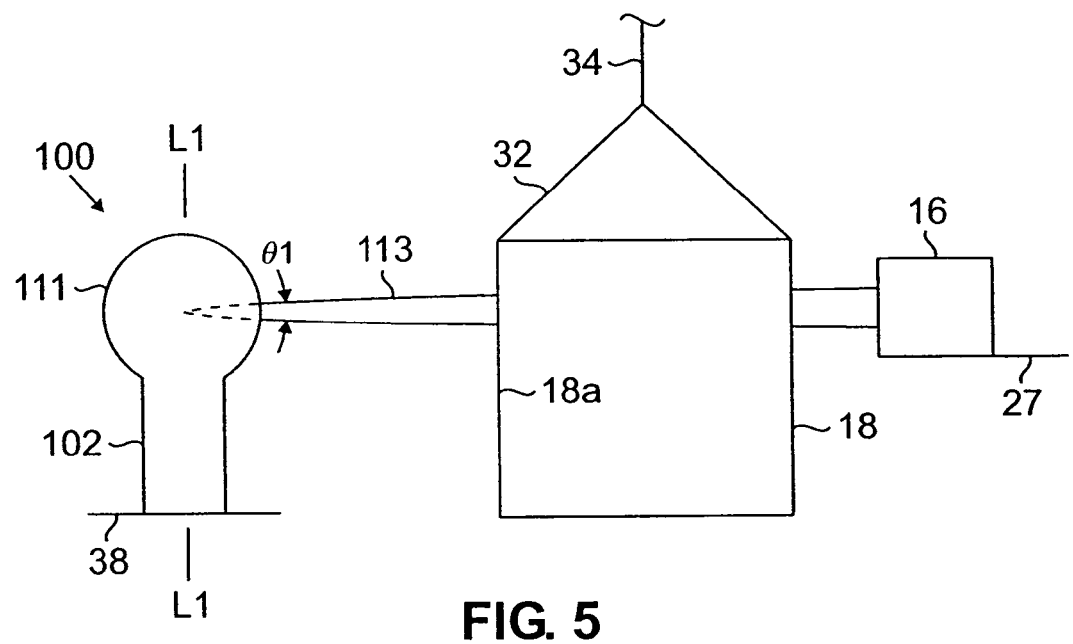
FIG. 5 is side view of the source of FIG. 3, in use in the radiation scanning system of FIG. 1.

FIG. 5 show the radiation source 100 with a shielded target 111 supported by the crane cross-beam 38, the detector 16 supported by a crane cross-beam 27 and a cargo conveyance 18 supported by a carriage 32 suspended from a metal rope 34. The remainder of the crane system 12 is not shown. The cargo conveyance 18 is being moved between the source 100 and the detector 34. The radiation source 100 is oriented with the longitudinal axis L1 of the accelerator body 102, vertical. To define a vertical height of a fan beam, the first angular dimension θ1 of the slot 112 may range from less than 1 degree to about 5 degrees. To define a vertical height of a cone beam, the first angulart dimension θ1 beam may range from about 5 degrees to about 45 degrees, for example. The second angular dimension θ2 may be any desired angle, such as any angle required to illuminate the entire width of the face 18a of the cargo conveyance 18. The angle may be 30 degrees or more, for example.

Figure 6:
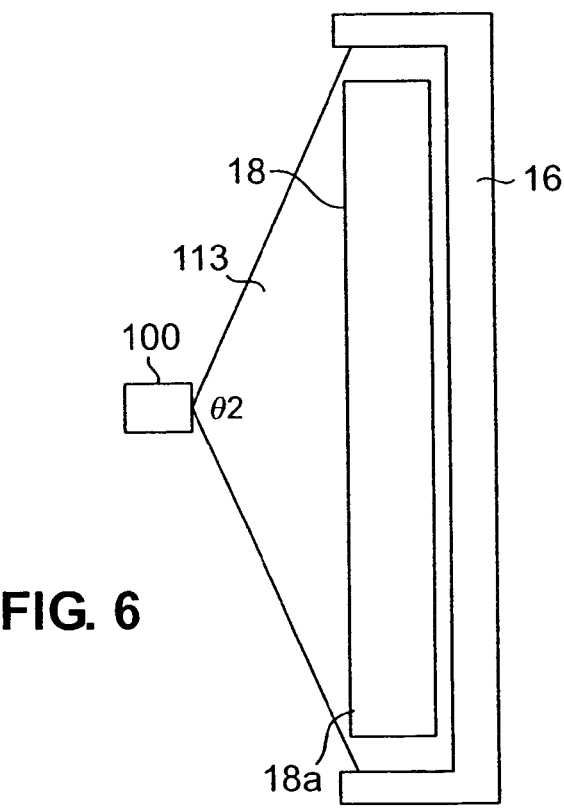
FIG. 6 is a top view of a cargo conveyance being lowered through a radiation beam emitted by the source of FIG. 3.

FIG. 6 is a top view of a cargo conveyance 18 being moved through a radiation beam 113 emitted by a panoramic radiation source 100. In this example, the second angular dimension θ2 is about 135 degrees. The source 100 may be about 8.5 feet (2.6 meters) from the face 18a of the cargo conveyance 18. Since the axis L1 of the accelerator body 102 is parallel to the face 18a of the cargo conveyance 18, the source 100 may be easier to support on a cross beam of the crane system 12.

Figure 7:
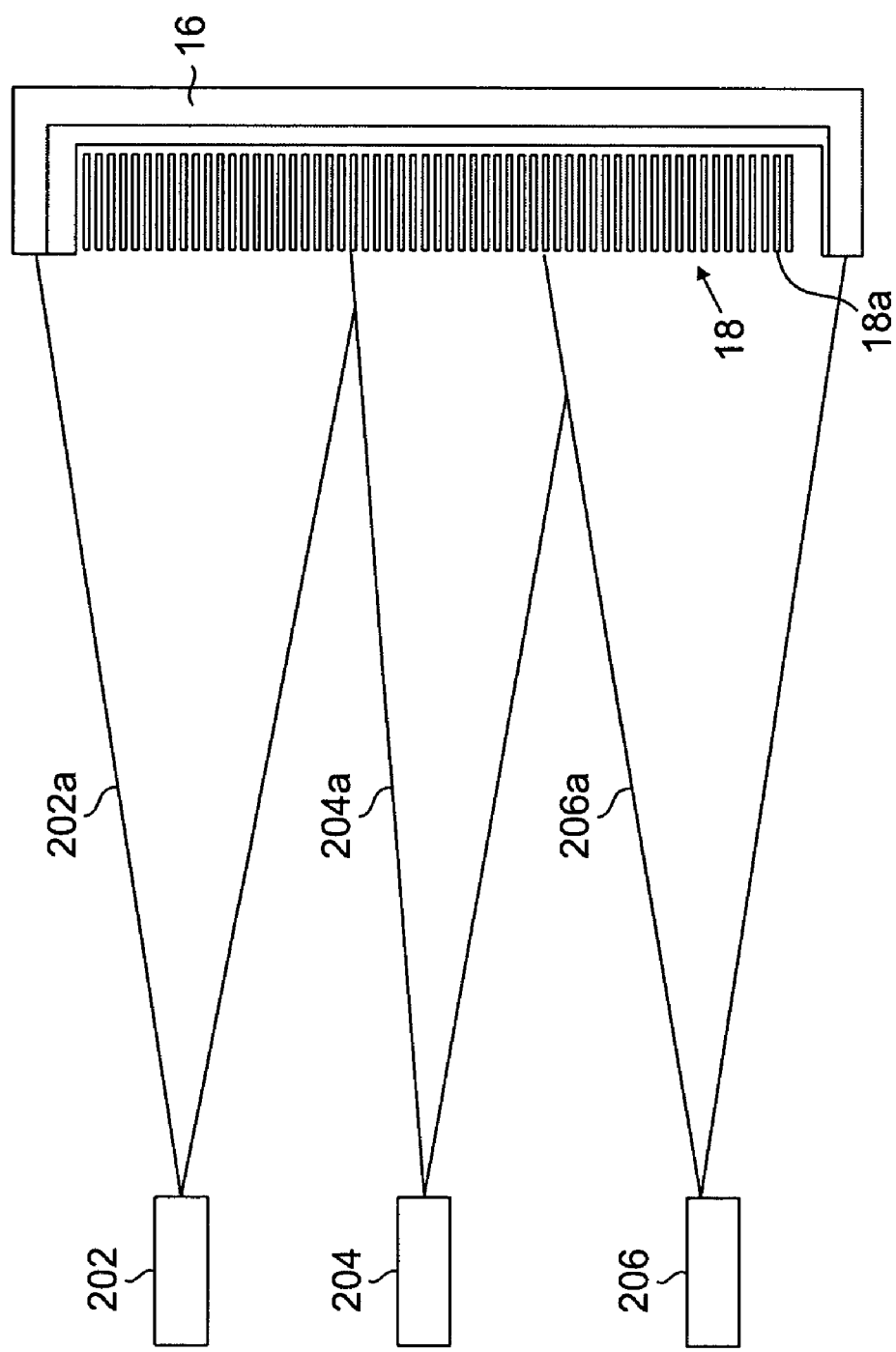
FIG. 7 is a partial top view of a cargo conveyance being lowered through three radiation beams emitted by three respective sources, in the embodiment of FIG. 1.

Instead of trying to cover the full length of the face 18a of the cargo conveyance 18 with a single, horizontally diverging radiation beam, as shown in FIGS. 2 and 6, multiple radiation beams may be to scan the entire face, with each beam scanning a portion of the face. In FIG. 7, multiple radiation sources 202, 204, 206 are provided, each emitting a respective radiation beam 202a, 204a, 206a illuminating a portion of the face 18a of the cargo conveyance 18. Each beam 202a, 204a, 206a preferably illuminates slightly more than one-third of the face 18a. It is preferred that each beam slightly overlap an adjacent beam, to ensure complete coverage of the face 18a. Each source emits a horizontally diverging radiation beam over an angle of about 10 degrees to about 30 degrees, for example. Each source 202, 204, 206 may be a linear accelerator, for example, such as the Varian Linatron® discussed above. The sources may illuminate the face simultaneously, or alternately. Alternating scanning by each source 202, 204, 206 is preferred. Each source 202, 204, 206 may alternately be on for one or a plurality of pulses within a data acquisition window of about 1 ms, for example. While three sources 202, 204, 206 emitting three beams 202a, 204a, 206a are shown, more or fewer sources and beams may be provided.

Since the angle each radiation beam 202a, 204a, 206a is emitted over is less than would be required if a single source 14, such as a single linear accelerator (see FIG. 2), was used, the entire cargo conveyance face 18 is exposed to a more uniform higher intensity radiation. In addition, the sources 202, 204, 206 may be closer to the face 18a, decreasing the intensity loss due to distance.

Figure 8:
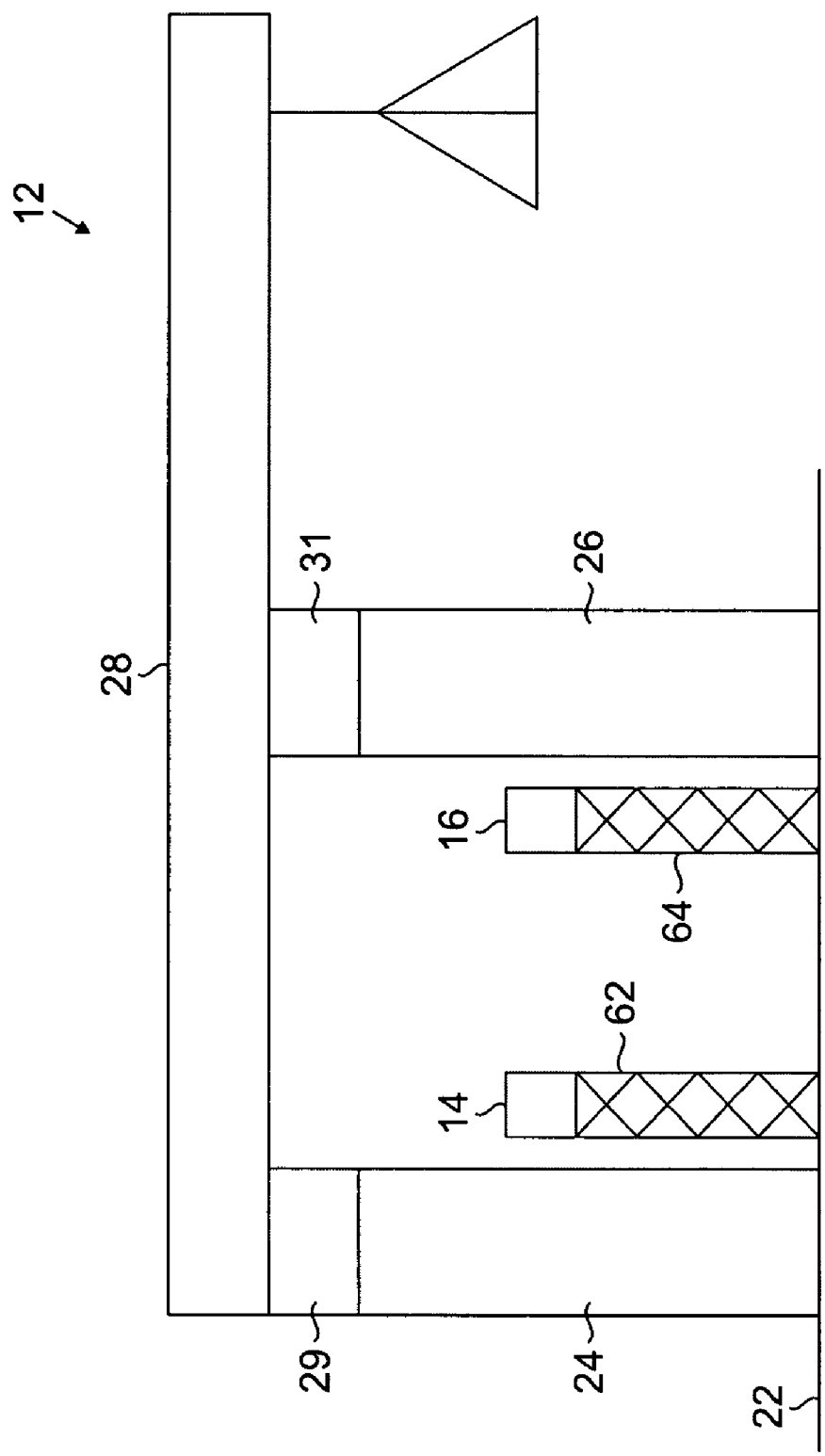
FIG. 8 is a side view of another embodiment of the invention, wherein a radiation source and a detector are supported by the ground proximate the crane system.
Figure 9:
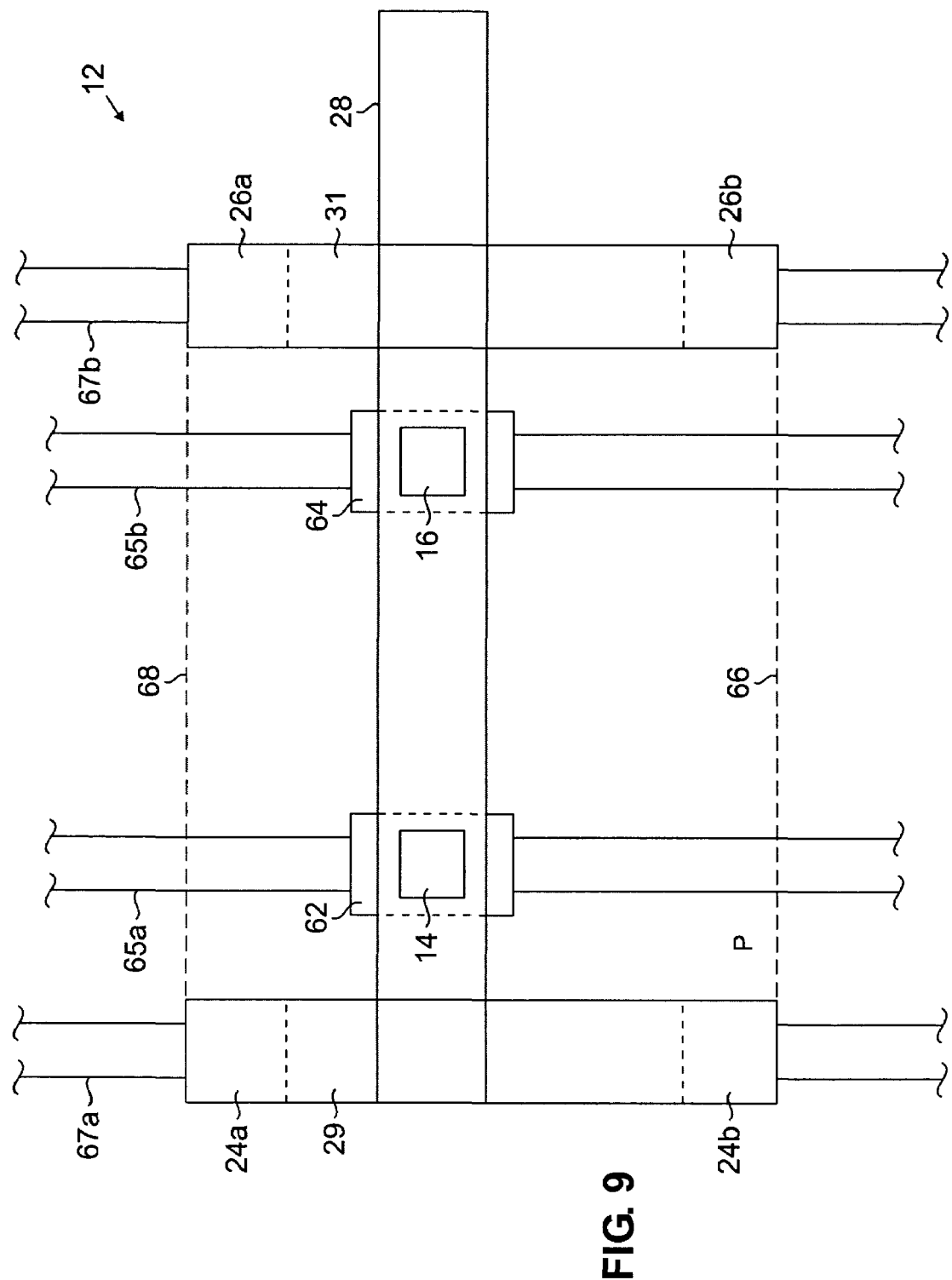
FIG. 9 is a top view of the embodiment of FIG. 8.

Instead of supporting the radiation source 14 and/or the detector 16 on the crane system 12, the source and the detector may be supported by the seaport 22, as shown in FIG. 8. The source 14 and/or detector 16 may be mounted on one or more supports 62, 64, respectively. The supports 62, 64 may be mobile. They may be movable along rails 65a, 65b on the seaport 22, for example, as shown in the top view of FIG. 9. The crane system 12 may be movable along rails 67a, 67b on the seaport 22, as well. Supporting the source 14 and/or the detector 16 by mobile supports 62, 64, facilitates the setup and precise positioning of the source 14 and the detector 16, regardless of the size of the crane system 12. FIG. 9 also shows the source 14 and detector 16 in a preferred position within a profile P of the crane system 12, defined by dotted lines 66, 68 and the vertical structures 24a, 24b, 26a, 26b, so that additional space is not taken up by the source and detector. However, the source 14 and detector 16 may be in any location through which the crane system 12 can move a cargo conveyance 18. For example, if the boom arm 28 is pivotable about a vertical axis, the cargo conveyance 18 may be moved through a location outside of the profile P of the crane system 12.

Figure 10:
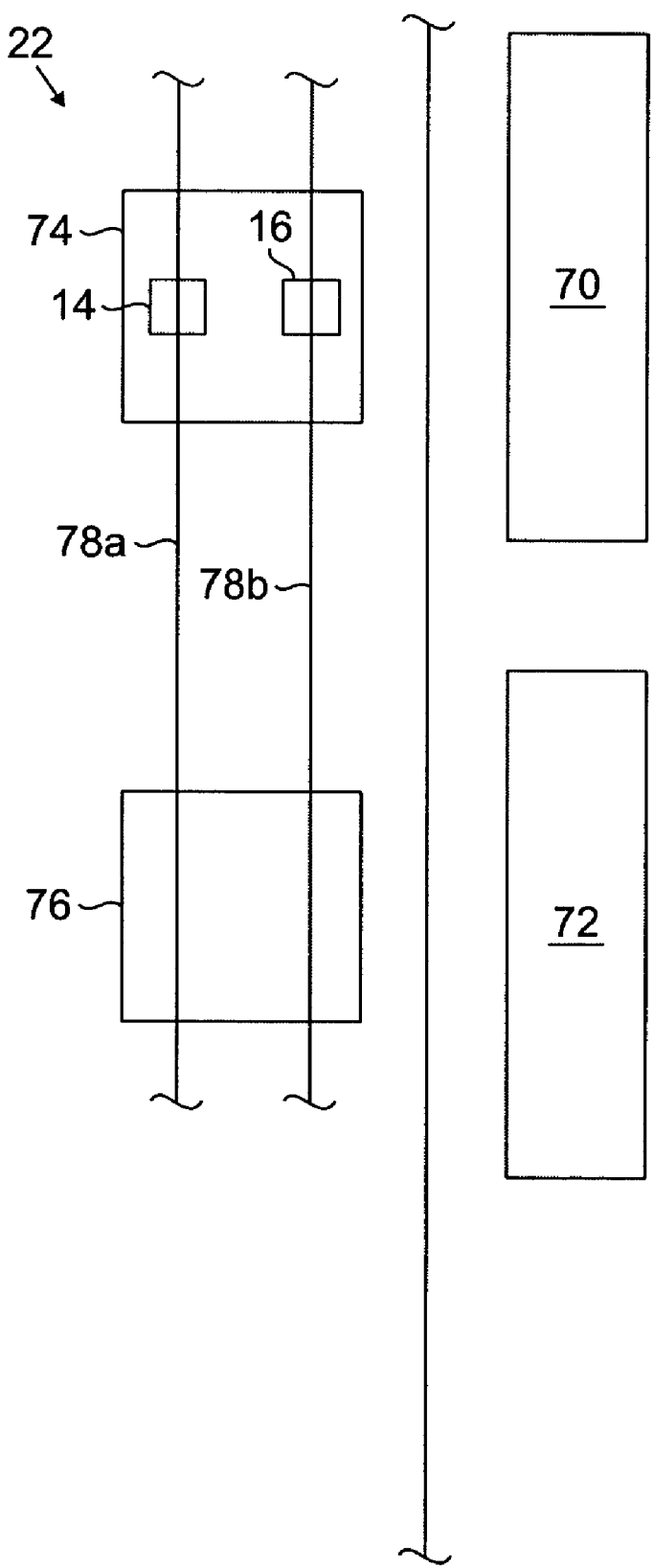
FIG. 10 is a top view of a seaport in accordance with an embodiment of the invention, incorporating the radiation scanning system of FIG. 8.

This embodiment of the invention enables a more efficient use of a radiation scanning system in a seaport. FIG. 10 is a top view of the seaport 22. Two ships 70, 72 are shown docked at respective docking stations of the seaport 22. Two crane systems 74, 76 are positioned at the docking stations, to unload or load cargo conveyances (not shown in this view) off of or onto the ships 70, 72, respectively. More docking stations may be provided, with a crane dedicated to each station. The source 14 and the detector 16 are shown movably supported on rails 78a, 78b, at the first docking station, to scan cargo conveyances being unloaded from or being loaded onto the ship 70. After completion of the unloading and loading of the ship 70, the source 14 and the detector 16 may be moved to the second docking station, to scan cargo conveyances being unloaded from or loaded onto the ship 72. Scanning may be coordinated among two or more stations so that the source 14 and detector 16 are at one station to scan cargo conveyances being unloaded from or loaded onto a ship, another ship is docking or preparing to be unloaded or loaded at the other station. One or a few radiation scanning systems may thereby be efficiently used to examine cargo conveyances being unloaded or loaded from or to multiple ships at the seaport, at lower cost, than mounting a radiation scanning system on each crane system. To move the source 14 and the detector 16, a conveying system may be provided along the rails 78a, 78b, for example.

While in the embodiments above, the cargo conveyance 18 is scanned while being lowered or raised, the conveyance may also be scanned while being moved horizontally (along arrow B in FIG. 1a, for example) by the conveying system 30. In that case, the radiation source 14 and the detector 16 may be supported by the crane system 12, or by supports 62, 64, so that they are aligned along an axis perpendicular to the horizontal direction of motion of the cargo conveyance 18. The source 14 may then emit a vertically diverging beam.

One of ordinary skill in the art will recognize that changes may be made to the embodiments described herein without departing from the spirit and scope of the invention, which is defined by the claims, below.

I claim:

1. A radiation scanning system for scanning objects comprising:
    a crane system to move an object from a first location to a second location, the object having a vertical height and a horizontal length greater than the vertical height;
    a radiation source proximate the crane system, configured to emit a horizontally diverging radiation beam having a width at a face of the object at least as long as the horizontal length of the object to irradiate the object; and
    a radiation detector proximate the crane system, positioned to receive radiation interacting with the object when the object is between the source and the detector;
    wherein the source and detector are positioned such that the object is movable vertically between the source and the detector by the crane system.

2. The radiation scanning system of claim 1, wherein the source is adapted to emit a fan beam.

3. The radiation scanning system in claim 1, wherein the radiation source is a source of X-ray radiation.

4. The radiation scanning system of claim 3, wherein the radiation source is adapted to emit a radiation beam having a peak energy of at least about 1 MeV.

5. The radiation scanning system of claim 4, wherein the radiation source is adapted to emit a radiation beam having a peak energy of at least about 6 MeV.

6. The radiation scanning system in claim 3, wherein the X-ray source is a linear accelerator.

7. The radiation scanning system of claim 1, wherein the detector and the source are aligned.

8. The radiation scanning system of claim 1, wherein at least one of the source or the detector are supported by the ground.

9. The radiation scanning system of claim 8, wherein the source and the detector are within a profile defined by the crane system.

10. The radiation scanning system of claim 8, wherein the ground is a seaport.

11. The radiation scanning system of claim 1, further comprising a guide in a space proximate the source and the detector, to guide the movement of the object between the source and the detector.

12. The radiation scanning system of claim 1, wherein the source comprises:
    a vertically oriented accelerator body having a distal end; and
    a shielded target at the distal end of the accelerator body, to emit a radiation beam towards the detector.

13. The radiation scanning system, claim 1, comprising:
    a plurality of sources proximate the crane system, each source adapted to emit a radiation beam upon a portion of an object between the source and the detector.

14. The radiation scanning system of claim 1, wherein the source and the detector are separated by a distance to scan a sea cargo conveyance.

15. The radiation scanning system of claim 1, wherein the crane system comprises:
    at least one vertical support;
    at least one horizontal support supported by the vertical support;
    a conveying system coupled to the horizontal support, to lift an object from a first location, move the object horizontally and lower the object to a second, different location.

16. The radiation scanning system of claim 1, further comprising:
    at least one rail;
    wherein at least one of the source or the detector are movably supported on the rail.

17. The radiation scanning system of claim 8, wherein:
    the at least one of the source or the detector is supported directly by the ground, independent of the crane system.

18. A radiation scanning system for scanning cargo conveyances, the system comprising:
    a crane system to move a cargo conveyance from a first location to a second location, the cargo conveyance having a horizontal length of at least 20 feet;
    a radiation source supported by the crane system; and
    a radiation detector supported by the crane system, positioned to receive radiation interacting with the cargo conveyance when the cargo conveyance is between the source and the detector;

wherein:
the source and the detector are positioned such that the cargo conveyance is moved vertically between the source and the detector by the crane system during scanning; and
the radiation source is configured to emit a horizontally diverging radiation beam having a width at a face of the cargo conveyance at least as long as the horizontal length of the cargo conveyance to irradiate the cargo conveyance.

19. The radiation scanning system of claim 18, wherein the source comprises:
a vertically oriented accelerator body to accelerate an electron beam, the accelerator body having a distal end; and
a shielded target at the distal end of the accelerator body, to emit a radiation beam towards the detector.

20. The radiation scanning system of claim 18, wherein the shielded target comprises:
a tube extending from the accelerator body to receive an electron beam accelerated by the accelerator body; and
a target material in the tube, to generate radiation upon impact by the electron beam; and
shielding material around the target, wherein the shielding material collimates the generated radiation into the horizontally diverging beam.

21. The radiation scanning system of claim 18, wherein the crane system comprises:
at least one vertical support;
at least one horizontal support supported by the vertical support;
a conveying system coupled to the horizontal support, to lift an cargo conveyance from a first location and lower the cargo conveyance to a second, different location.

22. The radiation scanning system of claim 20, wherein the conveying system is adapted to convey the cargo conveyance along a horizontal axis.

23. The radiation scanning system of claim 18, comprising:
a plurality of sources supported by the crane system, each source being adapted to emit a radiation beam upon a portion of the cargo conveyance.

24. The radiation scanning system of claim 18, wherein the radiation source is configured to emit a horizontally diverging radiation beam having a peak energy of at least 1 MeV.

25. A radiation scanning system comprising:
moving means for lifting a cargo conveyance from one location and lowering the cargo conveyance to a second location, the cargo conveyance having a horizontal length greater than a vertical height;
radiation generating means for generating a horizontally diverging radiation beam having a width at a face of the object at least as long as the horizontal length of the cargo conveyance; and
detecting means for detecting radiation interacting with the cargo conveyance;
wherein the moving means moves the cargo conveyance vertically between the generating means and the detecting means.

26. The radiation scanning system of claim 25, wherein:
the generating means generates a horizontally diverging radiation beam to irradiate the object while the moving means the object vertically.

27. A method of examining contents of an object, comprising:
moving an object along a first vertical axis, the object having a horizontal length greater than a vertical height;
moving the object along a second vertical axis different than the first vertical axis, through a horizontally diverging radiation beam having a width at a face of the object at least as long as the horizontal length; and
detecting radiation interacting with the object.

28. The method of claim 27, comprising:
lifting the object from a first location along the first vertical axis; and
lowering the object along the second vertical axis, through the radiation beam, to a second location.

29. The method of claim 28, wherein the object is a cargo conveyance, the first location is on a ship and the second location is on a seaport, the method comprising:
lifting the cargo conveyance from the ship; and
lowering the object through a radiation beam onto the seaport.

30. The method of claim 27, comprising:
lifting the object from a first location along the first vertical axis, through the radiation beam; and
lowering the object along the second vertical axis, to the second location.

31. The method of claim 30, wherein the object is a cargo conveyance, the first location is on a seaport and the second location is on a ship, the method comprising:
lifting the cargo conveyance from the seaport, through the radiation beam; and
lowering the cargo conveyance onto the ship.

32. The method of claim 27, comprising moving the object through a fan beam of radiation.

33. The method of claim 27, comprising moving the object through a cone beam of radiation.

34. The method of claim 27, comprising moving the object by a crane system.

35. The method of claim 27, further comprising:
moving at least one of a source of the horizontally diverging beam or a detector to detect radiation interacting with the object, into a position for operation.

36. A method of examining contents of a cargo conveyance, comprising:
moving a cargo conveyance having a horizontal length of at least about 20 feet by a crane system from a first location to a second location;
moving the cargo conveyance through a horizontally diverging radiation beam having a width at a face of the cargo conveyance at least as wide as the horizontal length of the cargo conveyance while moving the cargo conveyance at least part of the way from the first location to the second location; and
detecting radiation from an interaction of the cargo conveyance with the radiation beam.

37. The method of claim 36, comprising:
lifting the cargo conveyance by the crane system, from a first location;
lowering the cargo conveyance by the crane system, to a second location; and
scanning the cargo conveyance while lowering the cargo conveyance.

38. The method in claim 36, comprising:
lifting the cargo conveyance from a ship; and
lowering the cargo conveyance onto a seaport.

39. The method of claim 36, comprising:
lifting the cargo conveyance by the crane system, from a first location;
scanning the cargo conveyance while lifting the cargo conveyance; and
lowering the cargo conveyance by the crane system, to a second location.

40. The method of claim 39, comprising:
lifting the cargo conveyance from a seaport; and
lowering the cargo conveyance onto a ship.

41. The method of claim 36, further comprising:
moving the cargo conveyance horizontally between moving the cargo conveyance from the first location and moving the cargo conveyance to the second location.

42. The method of claim 41, comprising:
moving the cargo conveyance horizontally through the radiation beam.

43. The method of claim 36, further comprising:
moving at least one of a source of the radiation beam or a detector to detect radiation into position with respect to the crane system.

44. The method of claim 43, comprising:
moving at least one of a source of the radiation beam or a detector to detect radiation into position with respect to the crane system, along a respective rail.

45. A seaport comprising:
a plurality of docking stations;
a plurality of crane systems, each crane system being positioned at a respective docking station;
at least one rail through each docking station;
a radiation source; and
a radiation detector positioned to detect radiation emitted by the source and interacting with an object under examination;
wherein at least one of the source or the detector are movably supported on the rail, to move from one docking station to another.

46. The seaport of claim 45, wherein:
the source is adapted to generate a diverging radiation beam to irradiate the object.

47. The seaport of claim 46, wherein:
the source is adapted to generate a horizontally diverging radiation beam to irradiate the object.

48. The seaport of claim 45, further comprising:
at least one support movably supported on the at least one rail, to support the source and the detector.

49. The seaport of claim 48, comprising:
a first support movably supported on the at least one rail to support the source; and
a second support movably supported on the at least one rail to support the detector.

50. The seaport of claim 49, comprising:
at least two parallel rails, one to support the first support and the other to support the second support.

51. The seaport of claim 45, wherein the at least one rail extends through respective profiles of each crane system.

52. The method of claim 47, comprising:
generating the horizontally diverging radiation beam having a peak energy of at least 1 MeV.

53. A method of operating a seaport, comprising:
docking a first ship at a first docking station at a seaport;
moving a first object between the first ship and the seaport by a first crane at the first docking station;
scanning the first object by an X-ray system positioned at the first docking station;
docking a second ship at a second docking station at the seaport;
moving the X-ray system from the first docking station to the second docking station;
moving a second object between the second ship and the seaport by a second crane at the second docking station; and
scanning the second object by the X-ray station positioned at the second docking station.

54. The method of claim 53, comprising:
moving the X-ray system from the first docking station to the second docking station, along a rail.

55. The method of claim 53, comprising:
scanning first and second objects by respective diverging radiation beams.

56. The method of claim 55, comprising:
moving the first object vertically by the first cranes;
scanning the first object by a first horizontally diverging radiation beam while moving the first object;
moving the second object vertically by the second crane; and
scanning the second object by a second horizontally diverging radiation beam while moving the second object.

57. The method of claim 56, comprising:
moving the first object between a first truck on the seaport at the first docking station; and
moving the second object between a second truck at the seaport at the second docking station.

58. A radiation scanning system for scanning objects, comprising:
a crane system to move an object from a first location to a second location;
a radiation source proximate the crane system; and
a radiation detector proximate the crane system;
wherein:
the crane system moves the object between the radiation source and the radiation detector, during scanning; and
the source comprises:
a vertically oriented accelerator body having a distal end;
a target at the distal end of the accelerator body; and
shielding around the target, the shielding defining a slot therethrough, configured to emit a diverging radiation beam transverse to the vertically oriented accelerator body, towards the detector.

59. The radiation system of claim 58, wherein the slot is configured to define a horizontally diverging radiation beam.

60. The radiation scanning system of claim 58, wherein;
the object is a cargo conveyance having a horizontal length greater than a vertical height;
the source comprises a vertically oriented linear accelerator configured to generate radiation of at least 1 MeV; and
the slot is configured to define the diverging radiation beam with a width at a face of the cargo conveyance at least as wide as the horizontal length of the cargo conveyance.

61. The radiation scanning system of claim 60, wherein the cargo conveyance has a horizontal length of at least about 20 feet.

62. The radiation scanning system of claim 61, wherein the horizontal length is at least about 40 feet.

63. The radiation scanning system of claim 60, wherein the slot is configured to define a horizontally diverging radiation beam diverging over an angle of at least 30 degrees.

64. The radiation scanning system of claim 63, wherein the detector comprises:
a first detecting section facing the source; and
second and third detecting sections transverse to the first section.

65. The radiation scanning system of claim 64, wherein:
the first detecting section is straight; and
the second and third detecting sections are perpendicular to the first detecting section.

66. A radiation scanning system for scanning objects, comprising:
a crane system to move an object from a first location to a second location;
a radiation detector proximate the crane system; and
a plurality of radiation sources proximate the crane system, at least some of the radiation sources being adapted to emit a radiation beam only upon a respective portion of an object moved between the source and the detector by the crane system, to irradiate the entire object;
wherein the detector is positioned to detect radiation interacting with the object.

67. The system of claim 66, wherein:
the object is a rectangular container having a longitudinal face;
the crane system is adapted to move the container vertically, between the source and the detector, and through the radiation beams; and
the plurality of sources are positioned such that the entire longitudinal face of the container is irradiated while the container is moved vertically between the plurality of sources and the detector.

68. The radiation scanning system of claim 67, wherein:
the at least some of the radiation sources are configured to emit respective horizontally diverging radiation beams; and
the respective portions of the object partially overlap.

69. The radiation scanning system of claim 67, wherein the rectangular container is a cargo conveyance having a horizontal length of at least about 20 feet.

70. The method of claim 69, wherein the cargo conveyance has a horizontal length of at least about 40 feet.

71. A radiation scanning system for scanning objects, comprising:
a crane system supported by ground to move an object from a first location to a second location;
a radiation source proximate the crane system, to emit a radiation beam toward the object;
a radiation detector proximate the crane system; and
at least one rail, supported on the ground proximate the crane system;
wherein:
at least one of the source or the detector are movably supported by the rail such that the object may be moved between the source and the detector by the crane system.

72. A radiation scanning system for scanning objects, comprising:
a crane system comprising:
a boom arm lying in a plane, to move an object between a first location and a second location;
forward vertical supports to support the boom arm, the forward vertical supports being connected by at least one first crossbeam extending along a first axis substantially perpendicular to the plane; and
rearward vertical supports to support the boom arm, the rearward vertical supports being connected by at least one second crossbeam extending along a second axis substantially perpendicular to the plane;
a radiation source supported by one of the first or second crossbeams;
a radiation detector supported by another of the first or second crossbeams;
wherein:
the boom arm extends forward of the forward vertical support, to access the first location;
the second location is between the forward vertical supports and the rearward vertical supports; and
the boom arm moves the object vertically, between the radiation source and the radiation detector, during scanning.

* * * * *